US006846296B1

(12) United States Patent
Milbocker et al.

(10) Patent No.: US 6,846,296 B1
(45) Date of Patent: Jan. 25, 2005

(54) APPARATUS AND METHOD FOR DETACHABLY SECURING A DEVICE TO A NATURAL HEART

(75) Inventors: Michael T. Milbocker, Holliston, MA (US); Robert B. Stewart, Ipswich, MA (US); Robert L. Buck, Methuen, MA (US)

(73) Assignee: Abiomed, Inc., Danvers, MA (US)

( * ) Notice: Subject to any disclaimer, the term of this patent is extended or adjusted under 35 U.S.C. 154(b) by 199 days.

(21) Appl. No.: 09/661,885

(22) Filed: Sep. 14, 2000

(51) Int. Cl.[7] .............................................. A61H 31/00
(52) U.S. Cl. ........................ 601/153; 600/16; 623/3.16
(58) Field of Search ........................... 601/153; 600/16, 600/37, 375; 607/119, 126–131; 623/3.21, 3.16

(56) References Cited

U.S. PATENT DOCUMENTS

| 2,826,193 | A | 3/1958 | Vineberg |
| 3,464,322 | A | 9/1969 | Pequignot |
| 3,587,567 | A | 6/1971 | Schiff |
| 3,613,672 | A | 10/1971 | Schiff |
| 3,659,593 | A | 5/1972 | Vail |
| 3,674,019 | A | 7/1972 | Grant |
| 4,157,713 | A | 6/1979 | Clarey |

(List continued on next page.)

FOREIGN PATENT DOCUMENTS

| EP | 0370931 A1 | 5/1990 |
| FR | 2645739 A1 | 10/1990 |
| GB | 2115287 A | 9/1983 |
| JP | 2271829 | 11/1990 |
| SU | 1009457 A | 7/1983 |
| SU | 1734767 A1 | 5/1992 |
| WO | WO 94/21237 | 9/1994 |
| WO | 9922784 | 5/1999 |

OTHER PUBLICATIONS

Bencini et al. "The 'Pneumomassage' of the Heart," Surgery. Mar. 1956. 39:375–384. The National Medical Society.

Anstadt, G. et al. "A New Instrument for Prolonged Mechanical Cardiac Massage." Circulation. 1965. vol. 31 and 32, Supplement II, II–43II–44. Lippincott Williams & Wilkins.

Carpentier et al. "Myocardial Substitution with a Simulated Skeletal Muscle: First Successful Clinical Case." The Lancet. 1985. 1: 126. The Lancet Publishing Group.

Anstadt, Mark P. et al. "Direct Mechanical Ventricular Actuation: A Review." Resuscitation. 1991. 21: 7–23. Elsevier Science Inc.

Anstadt, Mark P. et al. "Pulsatile Reperfusion After Cardiac Arrest Improves Neurologic Outcome." Annals of Surgery 1991. 214(4): 478–490. American Surgical Association.

Capouya, Eli R. et al. "Girdling Effect of Nonstimulated Cardiomyoplasty on Left Ventricular Function." Ann. Thorac. Surgery. 1993. 56: 867–871. Elsevier Science Inc.

Carpetier et al. "Dynamic Cardiomyoplasty at Seven Years." The Journal of Thoracic and Cardiovascular Surgery. 1993. 106(1): 42–54. Mosby, Inc.

(List continued on next page.)

*Primary Examiner*—Justine R. Yu
*Assistant Examiner*—Victor Hwang
(74) *Attorney, Agent, or Firm*—Thomas J. Engellenner; Nutter McClennen & Fish LLP

(57) ABSTRACT

Methods and apparatus are disclosed for attaching cardiac devices onto a natural heart by employing arrays of gripping elements, such as hooks or barbs. The gripping elements are designed to penetrate and lodge themselves in the epicardial tissue in order to secure the device to at least a portion of the surface of the heart muscle. The gripping elements, although designed to penetrate the surface of the heart, have limited depth penetration so as to avoid puncture of blood vessels. The attachment mechanisms disclosed herein can also permit both attachment and detachment of device.

41 Claims, 14 Drawing Sheets

U.S. PATENT DOCUMENTS

| | | |
|---|---|---|
| 4,340,091 A | 7/1982 | Skelton et al. |
| 4,536,893 A | 8/1985 | Parravicini |
| 4,628,937 A | 12/1986 | Hess et al. |
| 4,690,134 A | 9/1987 | Snyders |
| 4,803,744 A | 2/1989 | Peck et al. |
| 4,827,932 A | 5/1989 | Ideker et al. |
| 4,902,291 A | 2/1990 | Kolff |
| 4,936,857 A | 6/1990 | Kulik |
| 4,957,477 A | 9/1990 | Lundback |
| 5,078,134 A | 1/1992 | Heilman et al. |
| 5,098,369 A | 3/1992 | Heilman et al. |
| 5,111,818 A | 5/1992 | Suzuki et al. |
| 5,119,804 A | 6/1992 | Anstadt |
| 5,131,905 A | 7/1992 | Grooters |
| 5,169,381 A | 12/1992 | Snyders |
| 5,243,723 A | 9/1993 | Cotner et al. |
| 5,300,110 A * | 4/1994 | Latterell et al. ............ 607/130 |
| 5,336,254 A | 8/1994 | Brennen et al. |
| 5,383,840 A | 1/1995 | Heilman et al. |
| 5,466,255 A * | 11/1995 | Franchi ...................... 607/128 |
| 5,534,024 A | 7/1996 | Rogers et al. |
| 5,558,617 A | 9/1996 | Heilman et al. |
| 5,564,142 A | 10/1996 | Liu |
| 5,611,085 A | 3/1997 | Rasmussen |
| 5,702,343 A | 12/1997 | Alferness |
| 5,704,891 A | 1/1998 | Mussivand |
| 5,707,336 A | 1/1998 | Rubin |
| 5,713,954 A | 2/1998 | Rosenberg et al. |
| 5,741,316 A | 4/1998 | Chen et al. |
| 5,800,528 A | 9/1998 | Lederman et al. |
| 5,853,005 A | 12/1998 | Scanlon |
| 5,902,229 A | 5/1999 | Tsitlik et al. |
| 5,971,910 A | 10/1999 | Tsitlik et al. |
| 5,991,665 A | 11/1999 | Wang et al. |
| 5,991,925 A | 11/1999 | Wu |
| 6,065,154 A | 5/2000 | Hulings et al. |
| 6,076,013 A | 6/2000 | Brennan et al. |
| 6,179,793 B1 | 1/2001 | Rothman et al. |
| 6,179,800 B1 | 1/2001 | Torrens |
| 6,212,430 B1 | 4/2001 | Kung |
| 6,221,103 B1 | 4/2001 | Melvin |
| 6,260,552 B1 * | 7/2001 | Mortier et al. ................ 600/16 |
| 2002/0188170 A1 * | 12/2002 | Santamore et al. ........... 600/37 |
| 2003/0065248 A1 * | 4/2003 | Lau et al. ..................... 600/37 |

OTHER PUBLICATIONS

Langer, Robert et al. "Tissue Engineering." Science, vol. 260, May 14, 1993, pp. 920–926.

Freed, Lisa E. et al. "Biodegradable Polymer Scaffolds for Tissue Engineering." Bio/Technology, vol. 12, Jul. 1994, pp. 689–693.

Checkanov, Valeri. "Nonstimulated Cardiomyoplasty Wrap Attenuated the Degree of Left Ventricular Enlargement." Ann. Thorac. Surg. 1994; 57: 1684–1685. Elsevier Science Inc.

Kass, David A. et al. "Reverse Remodeling from Cardiomyoplasty in Human Heart Failure: External Constraint Versus Active Assist." Circulation. 1995. 91(9): 2314–2318. Lippincott Williams & Wilkins.

Vaynblat, Mikhail et al. "Cardiac Binding in Experimental Heart Failure." Circulation. 1995. 92(8): I–380. Lippincott Williams & Wilkins.

Vaynblat, Mikhail et al. "Cardiac Binding in Experimental Heart Failure." Ann. Thorac. Surg. 1997. 64: 81–85. Elsevier Science Inc.

\* cited by examiner

APPARATUS AND METHOD FOR DETACHABLY SECURING A DEVICE TO A NATURAL HEART

BACKGROUND OF THE INVENTION

This invention relates to cardiac assistance devices and, more particularly, to devices designed to be secured to a natural heart for therapeutic or diagnostic purposes.

A major consideration in the design of cardiac assistance systems is the risk of thromboembolism or infection. These risks are heightened when the assist device includes blood-contacting surfaces. To avoid the need for direct blood contact, a class of devices known as "extra-cardiac assist devices" has been proposed. Extra-cardiac devices typically are implantable within the thoracic cavity and surround at least a portion of the patient's heart to provide therapy without directly contacting the patient's circulatory system.

A number of such implantable, extra-cardiac assist systems have been developed. These systems include active systems, which provide auxiliary pumping action to supplement or assist the blood pumping action of the natural heart, as well as passive systems, which support the heart without augmenting the natural heart's pumping action. Some cardiac assist devices are designed for short-term use (e.g., a few days) while others are intended for long term application (e.g., years). In many cases, it is also desirable that such devices be detachable.

For example, one class of active assist devices employs a heart-wrapping assembly formed of a flexible, but non-distensible, outer member with an elastic distensible inner membrane. An inflation fluid is then fed to one or more chambers defined between the non-distensible outer housing and the distensible inner membrane to effect pressure on the heart. In general, active assist devices fill and empty chamber(s) to compress the myocardium of the ventricle, and thus supplement the heart's natural pumping action.

There is considerable present interest in active cardiac assist devices that can be more easily applied to the heart. In emergency situations, the ability to quickly attach an extra-cardiac assist device to the heart can be critical to a patient's survival. Ideally, an extra-cardiac assist device should be quickly securable to the cardiac surface. It is likewise desirable for cardiac assist devices to be detachable without trauma to the heart and/or surrounding tissue.

Similar problems are encountered with passive cardiac assist devices, which have been proposed to prevent cardiac expansion beyond a predetermined volumetric limit in order to assist patients suffering from cardiac dilation or related conditions. In the absence of such constraint, the weakened heart muscle will deteriorate and lose its ability to pump blood. In passive devices, the goal is not to assist the natural heart's pumping action but rather to apply a constraining force during the heart's expansion (diastolic) phase.

Ideally, a passive device wrapped around the heart should mimic the natural resistance of the heart muscle itself to over-expansion. A healthy natural heart will exhibit a characteristic relationship between ventricular pressure and volume, such that small amounts of pressure at the beginning of diastole will initially result in a desired expansion of the ventricular volume. During activity or exercise, the ventricles must also respond to higher pressures to accommodate a greater volumetric expansion and, thereby, permit increased ventricular output. However, in certain disease states, the heart will increase in size over time beyond any normal volumetric range and then strain to pump blood. To arrest this dilation, which degrades cardiac performance, passive constraint devices have been proposed.

One problem that limits the effectiveness of passive devices is the need for such devices to maintain a close fit about the heart. Too loose a fit will degrade performance, while too tight a fit will put additional stress on the heart during diastolic expansion.

What is also needed is a passive cardiac device that can better mimic the heart's response to increases in diastolic pressure (in order to prevent further dilation) and, in particular, passive devices that can continue to function and respond to such pressures over time as the heart's function improves.

Conventional techniques and mechanisms for attachment of devices to the heart, such as sutures, glues, drawstrings and suction all have drawbacks, many of which directly contribute to the problems identified above. Sutures and drawstrings, for example, loosen over time and exacerbate the problem of maintaining a close fit of the device to the heart. Sutures can also cause trauma as a result of penetration into the myocardium. Suction can likewise cause trauma (e.g., hematomas) while glues can make it difficult to detach the device from the heart.

There exists a need for improved cardiac devices, generally, that can maintain contact with the beating heart (e.g., remain securely attached to the heart regardless of the state of pumping chambers or the heart itself—during both the diastole and systole phases.). This need for reliable attachment mechanisms applies not only to cardiac assist devices but to heart monitors, electrical sensors, pacemaker leads etc.

SUMMARY OF THE INVENTION

Methods and apparatus are disclosed for attaching cardiac devices onto a natural heart. The attachment methods and apparatus employ arrays of gripping elements, such as hooks or barbs, disposed on the surface of the devices. The gripping elements penetrate, and lodge themselves in, the epicardial tissue in order to secure the device to at least a portion of the surface of the heart muscle. The gripping elements secure the device to the surface of the heart, with limited depth penetration so as to avoid puncture of blood vessels or otherwise damaging or interfering with the function of the heart. The attachment mechanisms disclosed herein can also permit both attachment and detachment of device.

The present invention is useful, for example, in active extra-cardiac assist devices that are wrapped around the ventricles of an injured or diseased heart. When employed in connection with active devices, the gripping elements ensure that the device remains attached to the heart while the device provides contractile forces to assist in ventricular ejection. Similarly, the gripping elements of the present invention are useful with passive devices because they permit such passive devices to follow the natural contraction-relaxation cycle of the myocardium.

In one embodiment, the arrays of gripping elements can be arranged on pads that are attached to an inner surface of the device in order to attach the device to an exterior surface of the heart. The pads of gripping elements can be constructed as separate elements and then joined to an inner surface of the wrap element. Alternatively, the gripping elements and/or arrays can be formed as an integral part of the inner surface of the wrap element (e.g., the assist device and the gripping elements can form a unitary part).

In another aspect of the invention, the gripping elements can also be designed to facilitate removal of the device from the heart. For example, the gripping elements can be arranged such that the device can be slid (or twisted) into a position in which the gripping elements embed themselves into the heart surface and remain in such a "locked" position until subject to an opposite motion that unlocks or releases them. More generally, the gripping elements can be arranged to have one or more "restricted" directions along which movement of the device serves to attach the device to the heart, and at least one "unrestricted" direction that allows a clinician to pull or peel away the device.

BRIEF DESCRIPTION OF THE DRAWINGS

Other objects, advantages and features of the present invention will be readily appreciated and better understood by reference to the following detailed description when considered in connection with the accompanying drawings, in which like reference numerals designate like parts throughout the figures thereof and wherein:

In FIG. 5A, the initial deployment of the gripping surface is shown;

In FIG. 5B the gripping element is brought into contact with biological tissue and slid across the surface, such that the hook element is deformed;

In FIG. 5C the biological tissue continues to be slid across the surface such that the hook element is further deformed;

In FIG. 5D, the gripping element is slid backwards, such that the hook becomes set into the tissue;

In FIG. 6A, the initial deployment of the gripping surface is shown;

In FIG. 6B the gripping element is brought into contact with biological tissue and slid across the surface, such that the hook elements are deformed;

In FIG. 6C, the gripping element is slid backwards, such that both components of the opposing hooks become set into the tissue;

DETAILED DESCRIPTION

Figure 1:
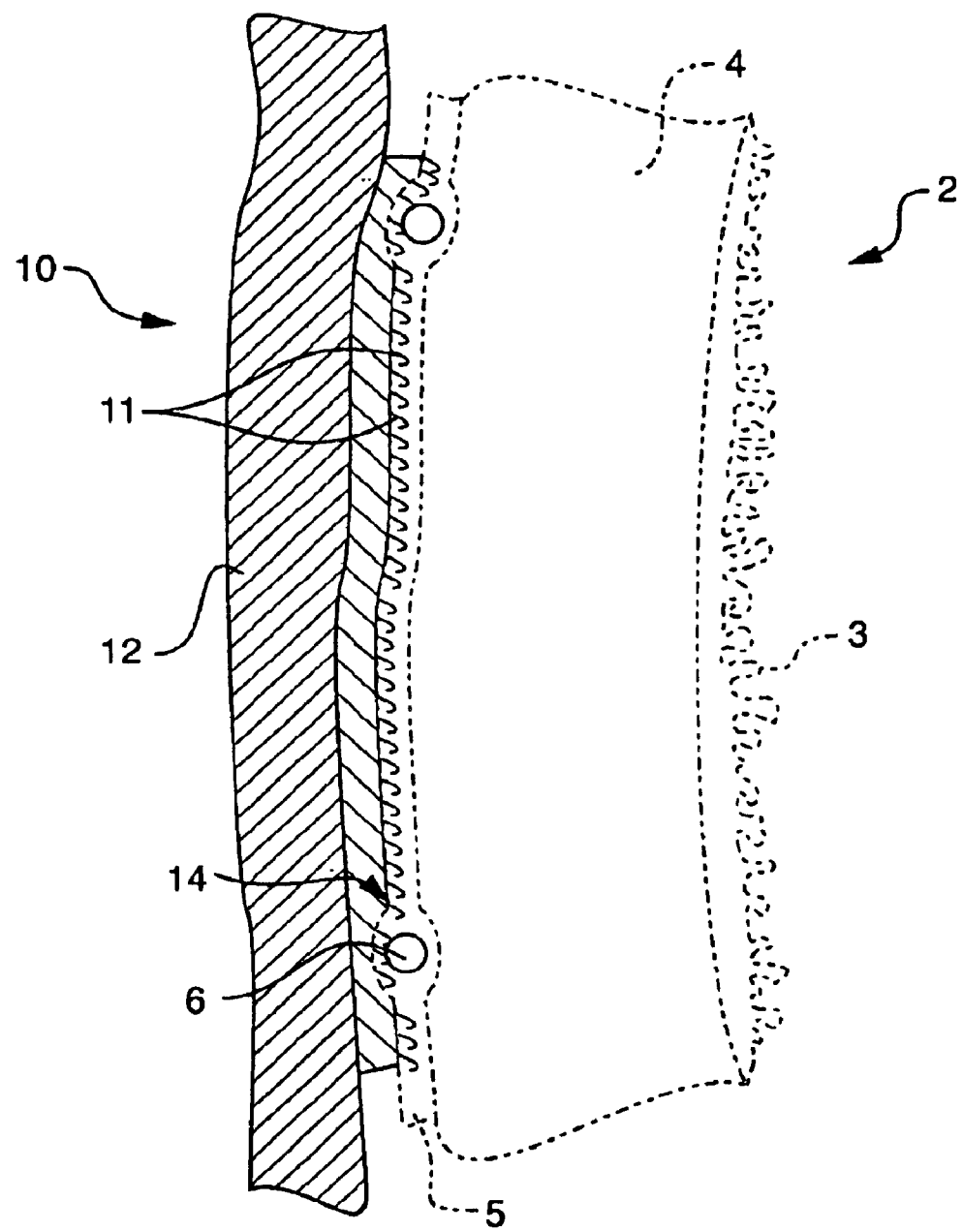
FIG. 1 is a schematic, cross-sectional illustration of an array of gripping elements applied to the surface of a heart, according to the invention.

FIG. 1 provides a schematic illustration of the function of the gripping elements 11 according to the invention. As shown, an array 14 of gripping elements 11 is attached to the surface 12 of a cardiac device 10 and engaged in contact with the surface of the heart muscle 2. In this simplified cross-sectional view of the heart, only the endocardium 3, myocardium 4 and epicardium 5 are shown. The gripping elements are preferably designed to lodge themselves within the epicardium 5 and secure the heart to the inner surface of the cardiac device 10. Thus, the gripping elements preferably have limited depth penetration, e.g., penetrating only the serous pericardium—the visceral layers of the epicardium. As further shown in FIG. 1, the outer surface of the heart muscle 2 also includes blood vessels 6. Preferably, the gripping elements 11 are designed to avoid puncturing such blood vessels.

The term "gripping element" as used herein is intended to encompass any object capable of penetrating and lodging itself in cardiac tissue, including but not limited to points, edges, protrusions, indentations, hooks, barbs and bristles. The term "gripping element" further encompasses elongate elements, generally, having a distal end for penetrating and attaching to cardiac tissue. Preferably the elongate elements are sized to penetrate less than 500 micrometers, or in the alternative, less than 300 micrometers, into cardiac tissue.

The term "hook" is likewise used broadly to mean any object or structure capable of lodging itself in cardiac tissue to provide an attachment. However, the gripping elements and hooks of the present invention are distinct from sutures, which require a strand or fiber to pierce biological tissue such that a loop of the suture material passed from a device, through the tissue and back again, in order to join the tissue to the device.

The term "cardiac tissue" as used herein encompasses the pericardium, epicardium, myocardium, fascia, blood vessels and any other tissue that comprises the external layers of the heart that can serve as substrate for attachment by griping elements according to the invention. The term "natural heart" is used to mean any non-mechanical heart, including a patient's own heart as well as transplanted hearts.

The term "vertically oriented" is meant to describe general alignment with the long axis of the heart (along an axis extending from the entry region of pulmonary veins to the apex of the heart). It is not intended to describe any specific fixed line or angle because of the variability of individual hearts.

Figure 2:
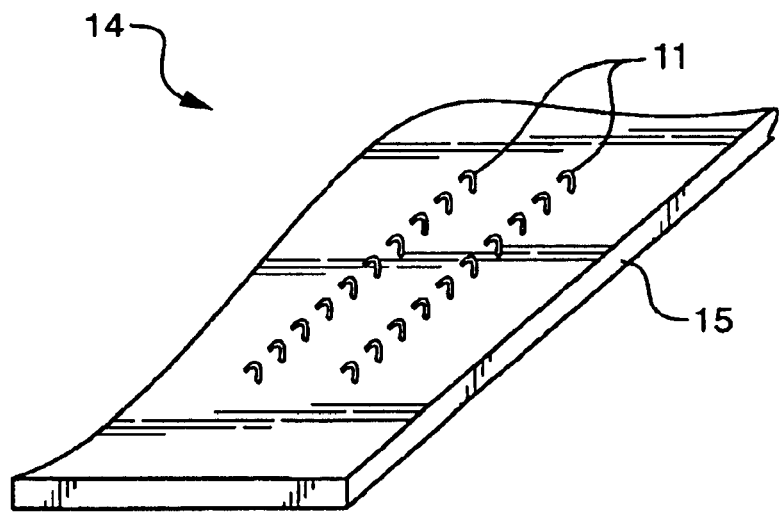
FIG. 2 is a schematic, perspective view of one type of gripping element according to the invention.

In FIG. 2 one embodiment of a gripping element 11 is shown composed of at least one hook structure 11 connected to a substrate 15, which can be rigid or flexible. (The hooks 11 and substrate 15 need not be separate elements but can be constructed as an integrated part, e.g., by casting or molding or laser machining.) The gripping element 11 can be formed by embedding hook-like elongate bodies into substrate 15 or by machining the substrate to form an array of hook structures designed to penetrate and grip the cardiac tissue.

Figure 3:
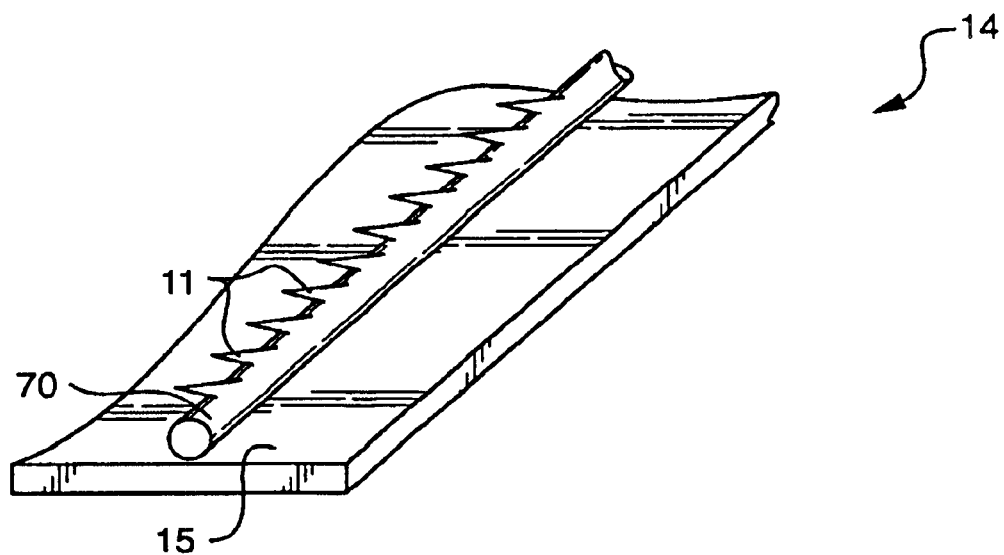
FIG. 3 is a schematic, perspective view of another type of gripping element according to the invention.

In FIG. 3 another embodiment of a gripping element 11 is shown composed of at least one wire-like structure 70 connected to a substrate 15. (Again, the wire 70 and substrate 15 need not be separate elements but can be constructed as an integrated part, e.g., by casting or molding or laser machining.) The gripping element 11 can be formed by shaving into the wire 70 to thus create a series of pointed structures to penetrate and grip the cardiac tissue.

Figure 4A:
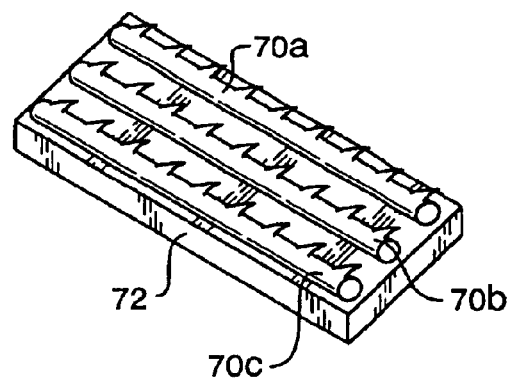
FIG. 4A is a perspective view of an array of gripping elements aligned with each other to create a gripping surface.

In FIG. 4A one array of gripping elements is shown in which a series of shaved wires 70A, 70B, and 70C, for example, are formed on the surface of the substrate 72 and aligned with each other to create a gripping surface (particularly preventing movement in one direction).

Figure 4B:
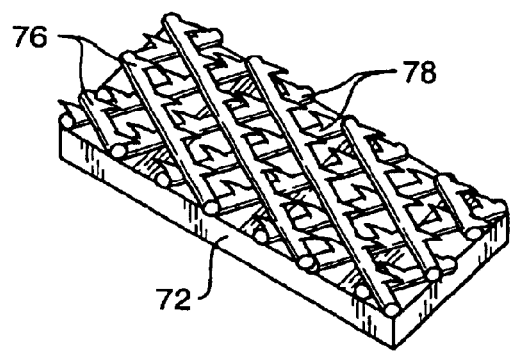
FIG. 4B is a perspective view of another array of gripping elements, which are disposed on the substrate and aligned in two different directions.

In FIG. 4B a similar array of gripping elements is disposed on the substrate 72. However, one set of barb strips 76 are arranged in one direction while a second set 78 of barb strips are arranged in a second direction at an angle from the first set 76.

Figure 4C:
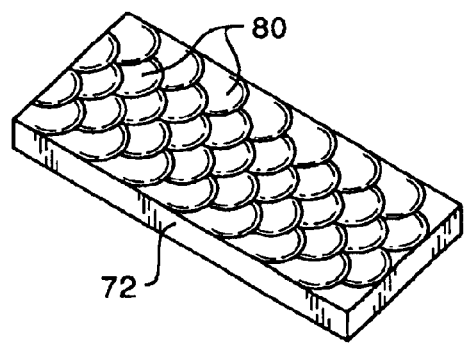
FIG. 4C is a perspective view of yet another embodiment of the gripping surface in which a series of fish scale-like protrusions are formed.
Figure 4D:
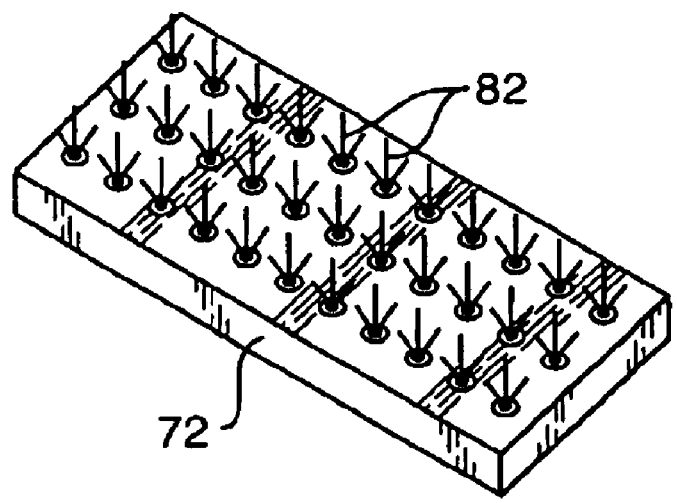
FIG. 4D is a perspective view of another embodiment of the gripping surface where a series of bristle-like elements are formed (or embedded) in a substrate material.
Figure 4E:
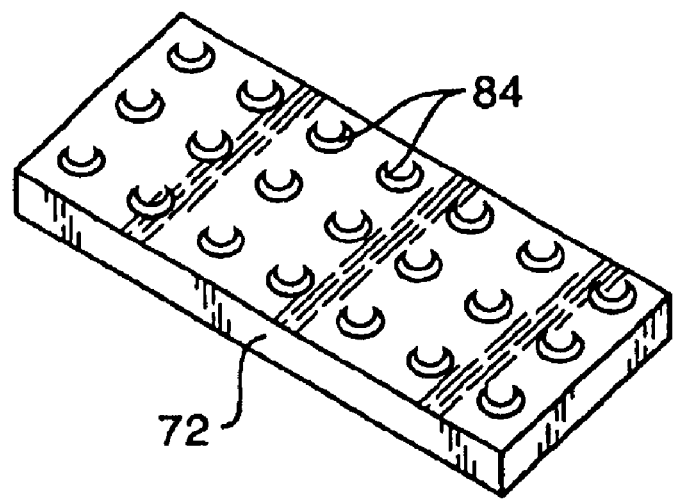
FIG. 4E is a perspective view of another embodiment of the gripping surface where a series of opposing hook elements are formed (or embedded) in a substrate material.

In FIG. 4C, yet another embodiment of the gripping surface is shown in which a series of fish scale-like protrusions 80 are formed on the substrate 72. Yet another embodiment of the gripping surface is shown in FIG. 4D where a series of bristle-like elements 82 are formed (or embedded) in a substrate 72 such that only a bristle-pointed region is exposed. Yet another embodiment of a gripping surface is shown in FIG. 4E where sets of opposing hooks are formed or attached to the substrate 72.

Figure 5A:
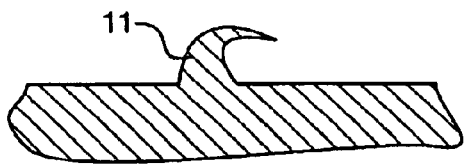
FIGS. 5A–5D illustrates the gripping action of the hook structures shown in FIG. 2.
Figure 5B:
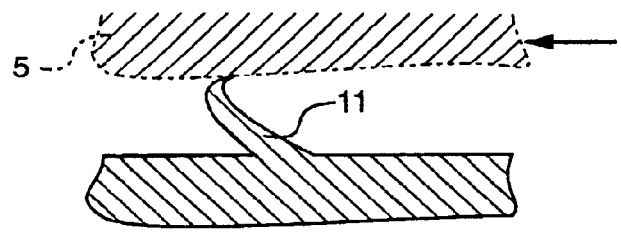
Figure 5C:
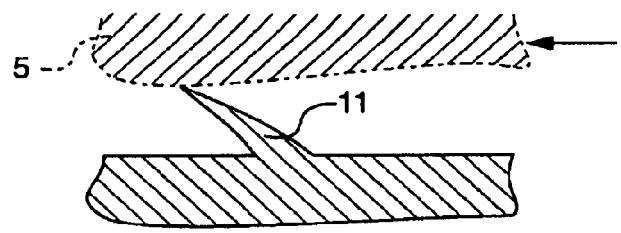
Figure 5D:
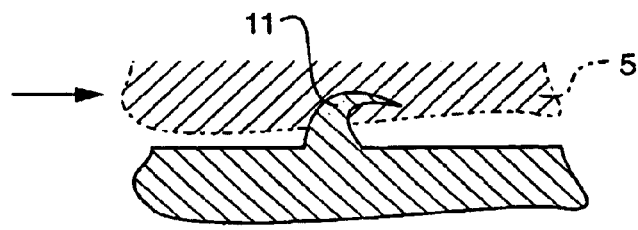

In FIGS. 5A–5D, the gripping action of the hook structures 11, shown in FIG. 2, is further illustrated. In this embodiment, the gripping surface includes a substrate 15 together with hook structures 11 as shown in FIG. 5A. When the gripping element is brought into contact with the epicardium 5 and slid across the surface in a first direction, the hook element 11 is deformed as shown in FIG. 5B and further deformed as shown in FIG. 5C. When the gripping element is slid backwards in an opposition direction, as illustrated in FIG. 5D, the hook 11 becomes set into the tissue 5.

Figure 6A:
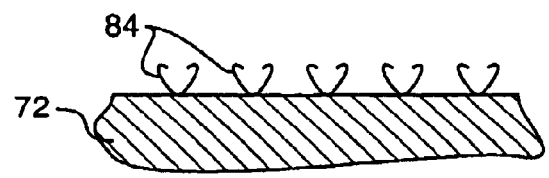
FIGS. 6A–6C illustrates the two-way gripping action of the opposing hook structures shown in FIG. 4E.
Figure 6B:
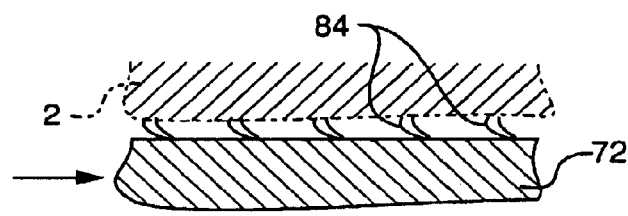
Figure 6C:
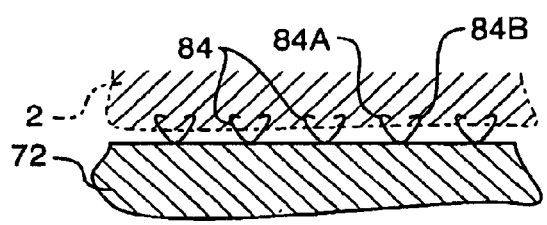

In FIGS. 6A–6C, the two-way gripping action of the opposing hook structures 84 shown in FIG. 7E is further illustrated. Again, as shown in FIG. 8A the gripping surface can include a substrate 72 together with sets of opposing hook structures 84. When the gripping element is brought into contact with biological tissue 2 and slid across the surface, the hook elements 84 are deformed, as shown in FIG. 6B. When the gripping element is slid backwards, as shown in FIG. 6C, both components of the opposing hooks 84A and B become set into the tissue 2.

Figure 7:
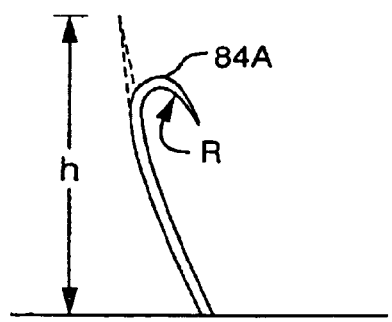
FIG. 7 is a more detailed illustration of a hook structure useful as a gripping element in accordance with the invention.
Figure 8A:
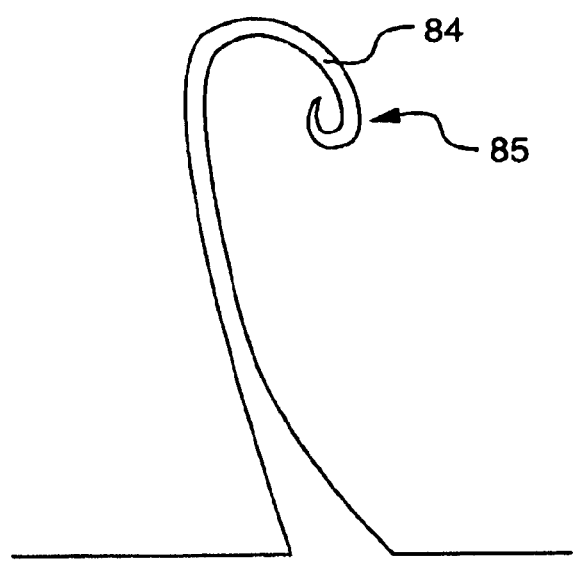
FIG. 8A is a more detailed illustration of another hook structure useful as a gripping element in accordance with the invention.
Figure 8B:
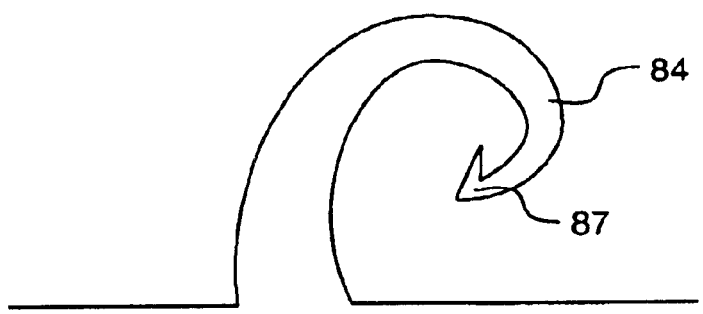
FIG. 8B is a more detailed illustration of yet another hook structure useful as a gripping element in accordance with the invention.

A more detailed illustration of a hook element is shown in FIG. 7. The hook is preferably designed such that the radius R is about 100 to about 500 micrometers and, in some applications, preferably less that 200 micrometers, while the overall height H of the hook element can range from about 0.2 to about 3.0 millimeters, and preferably about 0.5 to about 1.5 millimeters. FIG. 8A shown another embodiment of a hook element 84 with a more coiled tail region 85 that makes the gripping element more difficult to remove. Similarly, the gripping strength can also enhanced, as shown in FIG. 8B, by forming a hook element with a barb 87 at its distal end. By adjusting the parameters R and H, the flexibility and/or penetration depth of the hooks can be modified for particular applications.

It should be appreciated that all of the gripping elements of the present invention need not secure themselves to the heart when the cardiac devices are initially implanted. Some of the gripping elements may engage immediately while others will not. However, following implantation, the gripping elements become more "settled" and more attached to the heart as it beats. In contrast to prior art devices that tend to loosen over time, the attachment mechanisms of the present invention can actual improve over time.

For example, the hook height and the radius of curvature can be chosen such that the amount of movement necessary for the hook to penetrate into the epicardium is less than or equal to the amount of vertical displacement (in the case of a wrapped cardiac assist device) of the heart in the vertical direction when the heart contracts. A device with such an array of gripping elements can simply be placed around the heart and the heart's beating will cause the device to become attached to the heart.

Figure 9A:
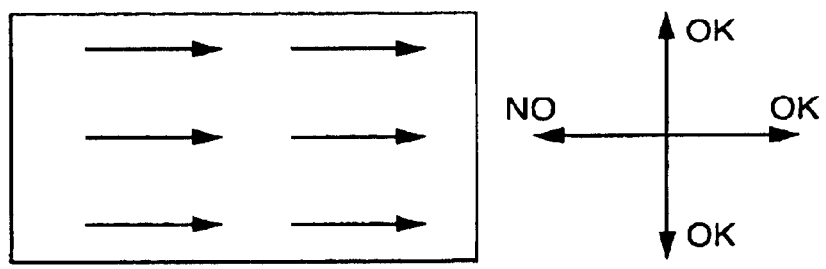
FIG. 9A is a schematic illustration of an arrangement of gripping elements oriented such a device with such pads has one translational direction of restricted motion.

FIG. 9A is a schematic illustration of an arrangement of gripping elements oriented such a device with such pads has one translational direction of restricted motion. In one embodiment, this can be achieved by orienting all of the gripping elements (e.g., the hooks or barbs) in one direction. Once the gripping elements have been "set" (e.g., lodged in the epicardial tissue), further movement in that direction is restricted. However, movement in the opposite direction (or to an extend in other directions) is relatively unencumbered. This arrangement permits the gripping elements of the present invention to not only provide a mechanism for attachment but also to permit detachment by appropriate movement of the array in at least one "unlocking" direction.

Figure 9B:
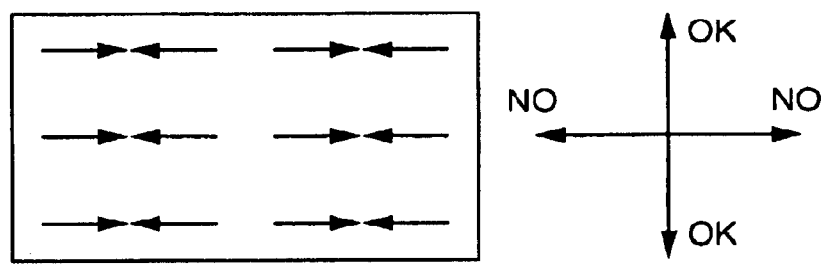
FIG. 9B is a schematic illustration of an arrangement of gripping elements oriented such a device with such pads has two directions of restricted motion.

FIG. 9B is a schematic illustration of an arrangement of gripping elements oriented such a device with such pads has two directions of restricted motion. In this embodiment, movement is restricted in both directions along one axis, while motion is relatively unrestricted in other (e.g., orthogonal) directions. The two-way restriction can be accomplished, as shown, by arranging the gripping elements in opposing pairs. Of course, a random arrangement of gripping elements can also be used to provide restricted motion in all directions.

Figure 9C:
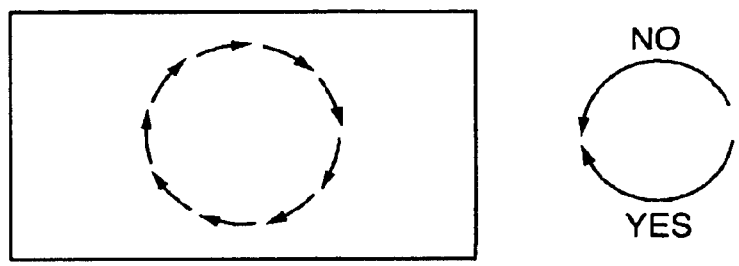
FIG. 9C is a schematic illustration of an arrangement of gripping elements oriented such a device with such pads has one rotational direction of restricted motion.

FIG. 9C is a schematic illustration of an arrangement of gripping elements oriented such a device with such pads has one rotational direction of restricted motion. In this embodiment, counterclockwise movement is restricted, while clockwise motion is relatively unrestricted. The rotational restriction can be accomplished, as shown, by arranging the gripping elements in a circular pattern. This embodiment is particularly useful for cup-like structures (e.g., as a replacement for the vacuum cups described below).

Figure 10:
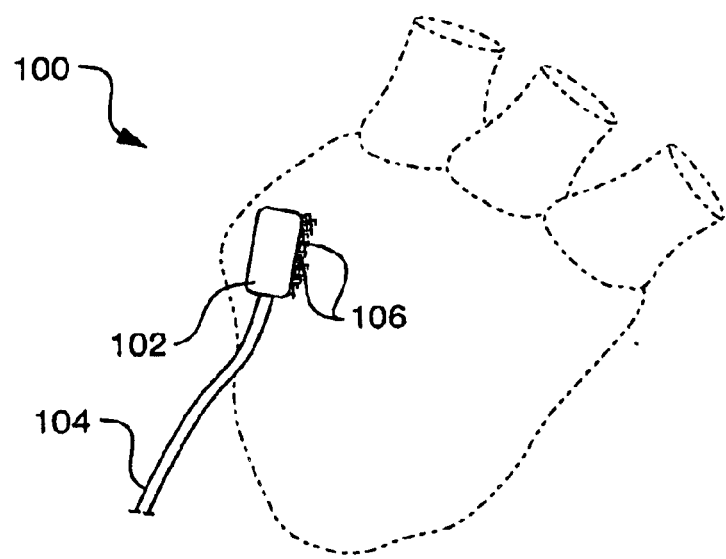
FIG. 10 is a schematic, perspective illustration of an electrode sensor device for monitoring electrical activity of the heart, which incorporates an attachment mechanism in accordance with one aspect of the invention.
Figure 10A:
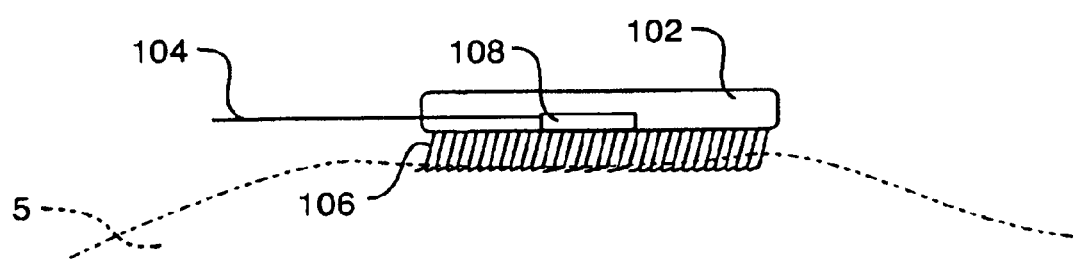
FIG. 10A is a cross-sectional view of the sensor of FIG 10.

FIG. 10 is a schematic, perspective illustration of an electrode sensor device 100 for monitoring electrical activity of the heart, employing the gripping elements of the present invention. As shown, the sensor 100 includes a body 102 and electrical leads 104, and gripping elements 106. FIG. 10A is a cross-section view of the sensor of FIG. 10 showing the electrode pad 108 which receives electrical signals and transmits them via leads 104 to a monitoring system (not shown). Alternatively, pad 108 can deliver electric currents or pulses to the heart. In addition, the gripping elements 106 can be conductive and coupled to the electrical leads 104 to serves as electrodes together with, or in lieu of, pad 108.

Figure 11:
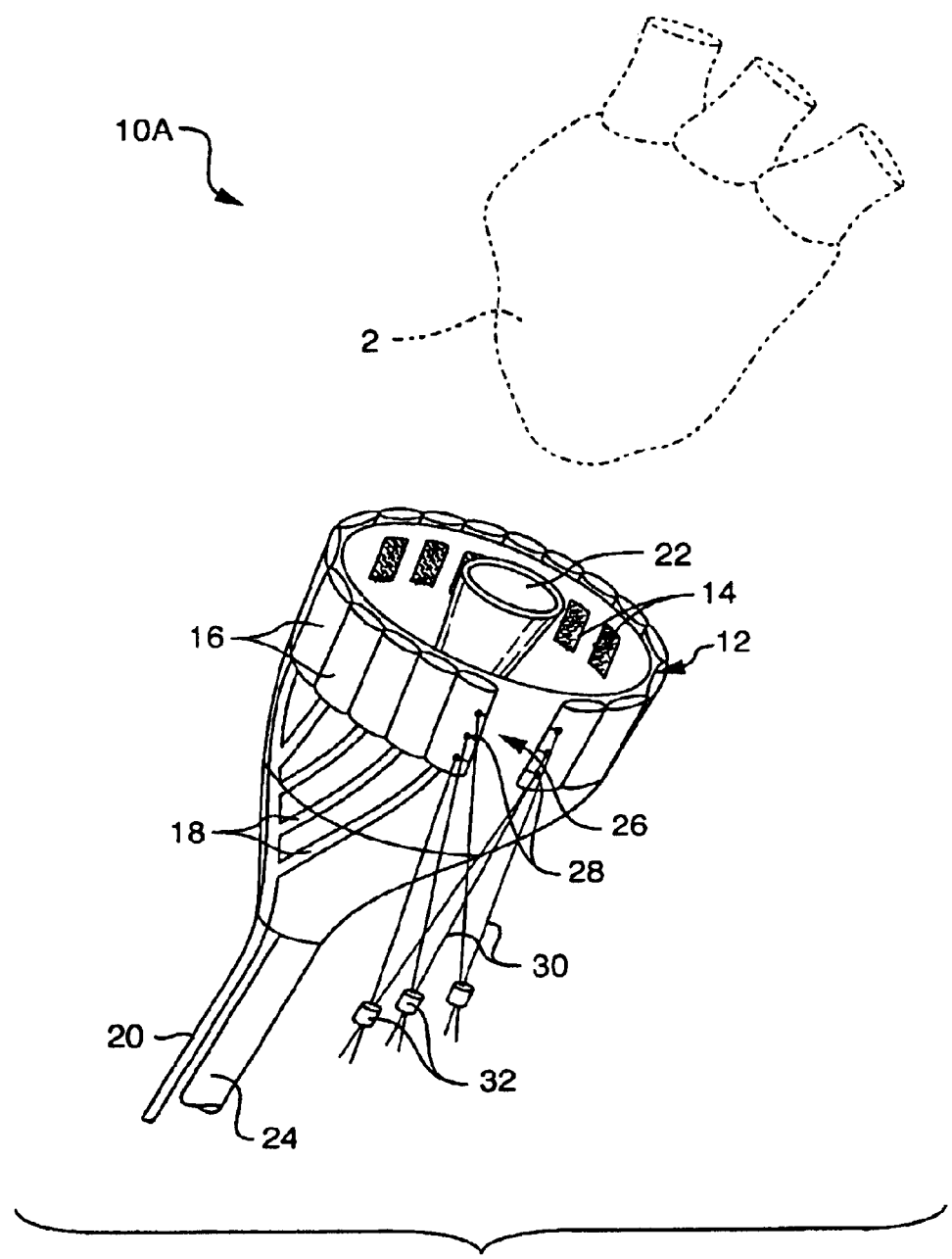
FIG. 11 is a schematic, perspective view of an active assist device with attachment mechanisms according to another aspect of the invention.

FIG. 11 shows an extra-cardiac assist device 10A for use in assisting the blood pumping action of a heart 2. The assist device 10A includes a wrap element 12 having a series of gripping element arrays 14, according to the invention. The device 10A further includes a plurality of inflatable chamber segments 16 which are connected via inflation lines 18 to a conduit 20 which serves as a source of inflation fluid. The assist device 10A mimics the contraction-relaxation characteristics of the natural myocardium and provides sufficient contractility, when actuated, to at least equal the contractility of a healthy natural myocardium. The device can be actuated by fluid pressure that is synchronized with the contractions of the natural heart. Using this system, the natural heart is left in place and the assist system supplies the timed reinforcing contractile forces required for satisfactory ventricular ejection and/or provide circulatory support to a fibrillating or arrested heart.

The wrap element can be a cuff formed of a series of closed tubes connected along their axially extending walls. By hydraulically (or pneumatically) inflating and deflating these tubes, a controlled circumferential contraction is produced as a result of the geometric shape of the tubes in deflated condition and the shape of tubes when they are filled in the inflated condition. If this cuff is wrapped around the natural heart, it will shorten circumferentially and squeeze the heart, when pressurized, by producing a "diastolic" to "systolic" toroidal diameter change.

The term "toroidal" as used herein is intended to encompass a variety of geometric shapes, not necessarily having a circular or elliptical inner opening. In fact, the toroidal shape of the cardiac wrap is likely to be somewhat irregular because of the asymmetric shape of the natural heart. "Toroidal" is meant to describe constructions that have an inner opening that can surround a portion of the heart. The cross-sectional shape of the wrap itself need not be doughnut-like (and will more often be band-like). In addition, the toroid need not be closed and, in some embodiments as described herein, will be open to accommodate different sized heart muscles.

Suitable hardware, including a hydraulic pump, a compliant reservoir and rotary mechanical valve, together with appropriate actuating electronics can all be implanted in the patient's body. If the power source is an internal battery, then power may be transcutaneously transmitted into the body to recharge this battery. For more details on the construction of extra-cardiac assist devices, see commonly owned, U.S. Pat. No. 5,713,954 issued to Rosenberg et al. On Jun. 13, 1995, herein incorporated by reference. See also, U.S. Pat. No. 5,119,804 issued to Anstadt on Jun. 9, 1992; U.S. Pat. No. 5,902,229 issued to Tsitlik on May 11, 1999; U.S. Pat. No. 5,971,910 issued to Tsitlik on Oct. 26, 1999, and U.S. Pat. No. 5,702,343 issued to Alferness on Dec. 30, 1997. The disclosures of all references cited in this specification are specifically incorporated by reference.

The device 10A of FIG. 11 can further include a suction cup 22 that is attachable to the apex of the heart temporarily to aid in device placement. Suction can be provided to the cup in order to hold the heart in place via central shaft 24 while the assist device is positioned about the heart. If desired, a cup incorporating the gripping elements of the present invention can replace the suction cup. The cardiac wrap 12 with its gripping elements 14 and chamber segments 16 can be slidably mounted about the central shaft such that the wrap can be moved axially into position about the heart after it is secured by the cup 22.

Figure 12:
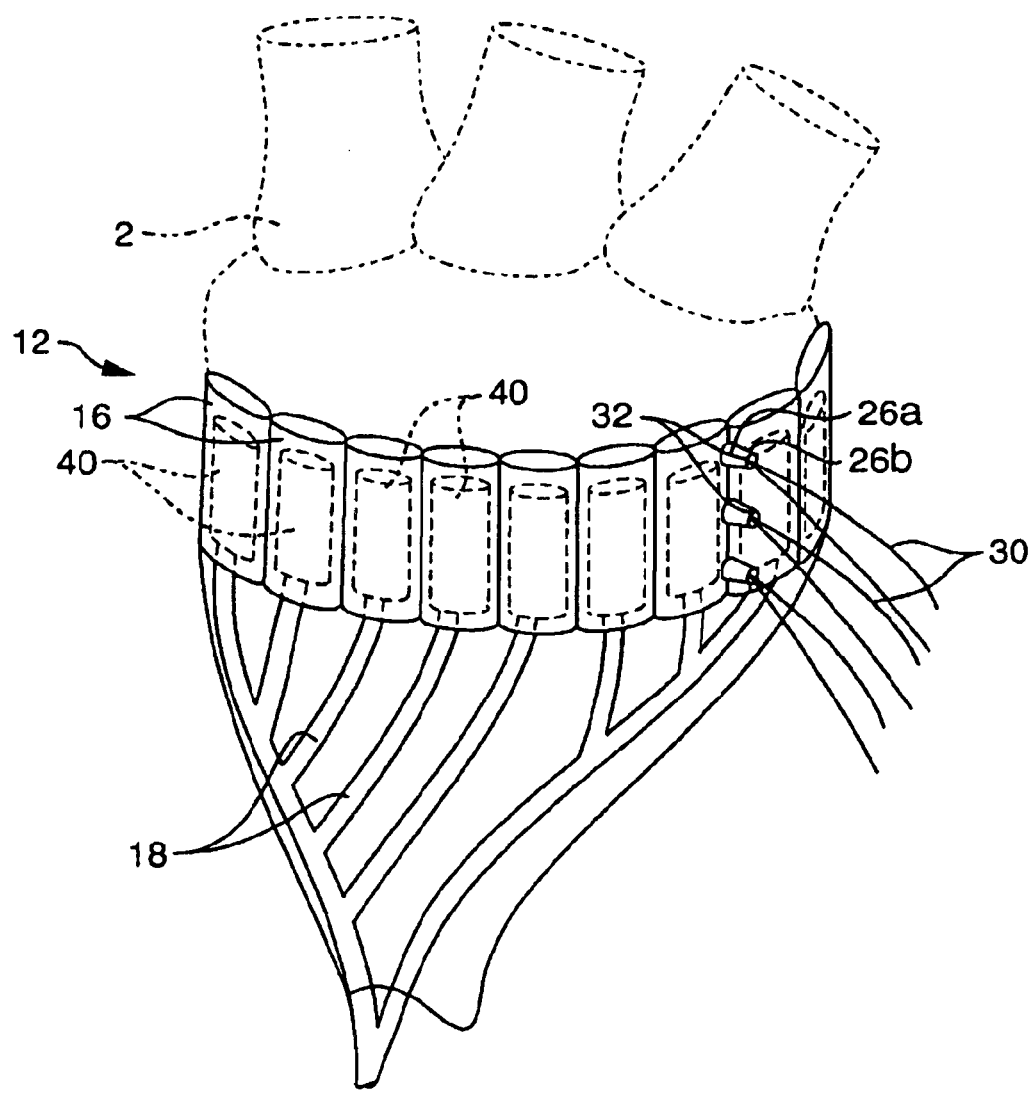
FIG. 12 is a schematic, perspective view of the extra-cardiac assist device of FIG. 11 disposed about a heart.

The wrap element 12 can be constructed with an opening or slit 26 to further accommodate the proper disposition of the device about the heart. The opening 26 in the wrap can be closed via drawstrings 30 that are connected to closures 28. The wrap element can be snugly situated about the heart, for example, by moving a cinch element 32 upward to a position at or near the opening 26. In the "closed" position, the wrap element 14 can be drawn tightly around the heart, as shown in more detail in FIG. 12. Also shown in FIG. 12 are a plurality of inflation tubes 40 which can be disposed within the wrap element 12 in order to define a series of inflatable chambers.

Figure 13:
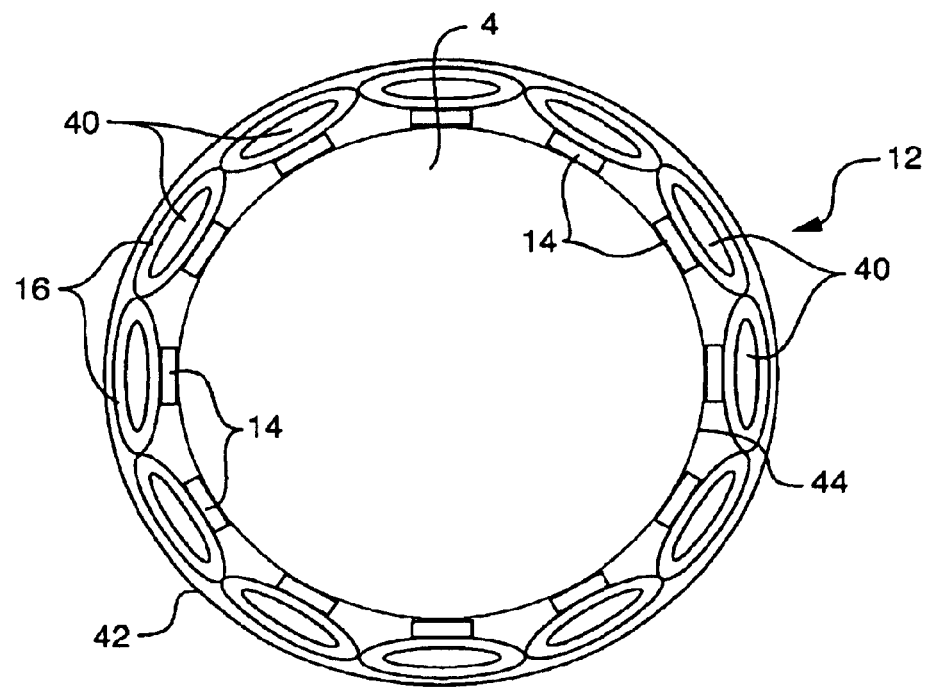
FIG. 13 is a cross-sectional view of an active extra-cardiac assist device according to the invention in an uninflated toroidal state having a relatively large inner diameter.

FIG. 13 is a cross-sectional cup view of the extra-cardiac assist device 10 of the present invention in an uninflated state about a heart. In this uninflated state the inner wall of the wrap element defines an inner diameter 44 and an inner space roughly equal to the cross-sectional area of the heart muscle during its diastolic (expanded) state. A plurality of gripping elements 14 are disposed on the inner wall of the wrap 12 to contact the surface of the heart muscle and, thereby, secure it to the wrap element 12 of the assist device 10. In FIG. 13, the inflatable tube elements 40 are shown in a nearly flat, uninflated state within outer diameter 42 of the device.

Figure 14:
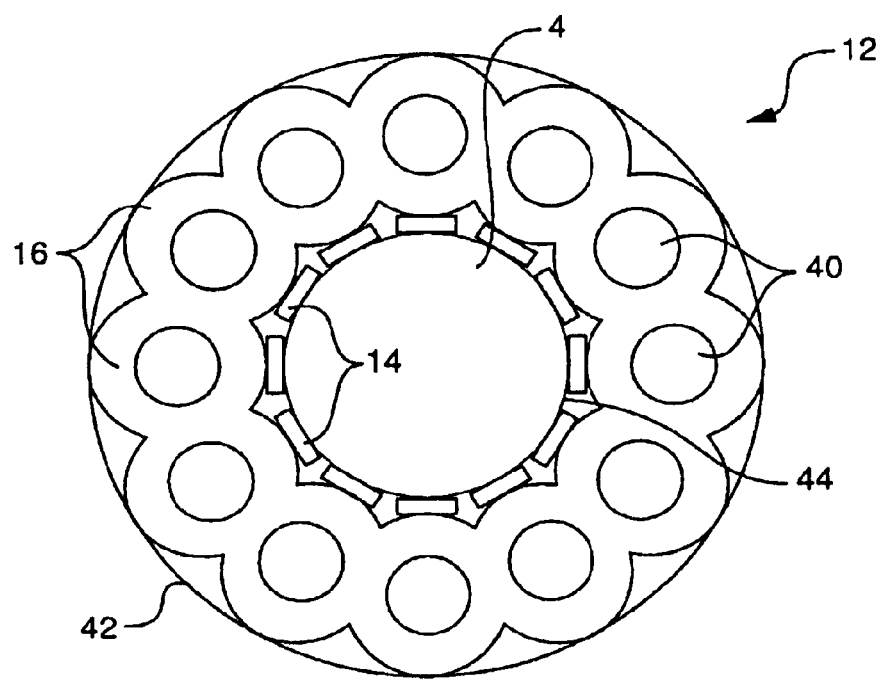
FIG. 14 is cross-sectional view of an extra-cardiac assist device of FIG. 13 in an inflated toroidal state having a smaller inner diameter.

In FIG. 14 an inflation fluid has been introduced to fill the inflatable chambers defined by the tubes 40. As a result of inflation, outer diameter 42 is unchanged, but the inner diameter 44 of the device undergoes a substantial reduction. Consequently the enclosed volume 4 is compressed, thus, providing an assist to the heart during systolic pumping. The gripping elements of the present invention secure the device to the heart throughout the entire cycle.

Figure 15:
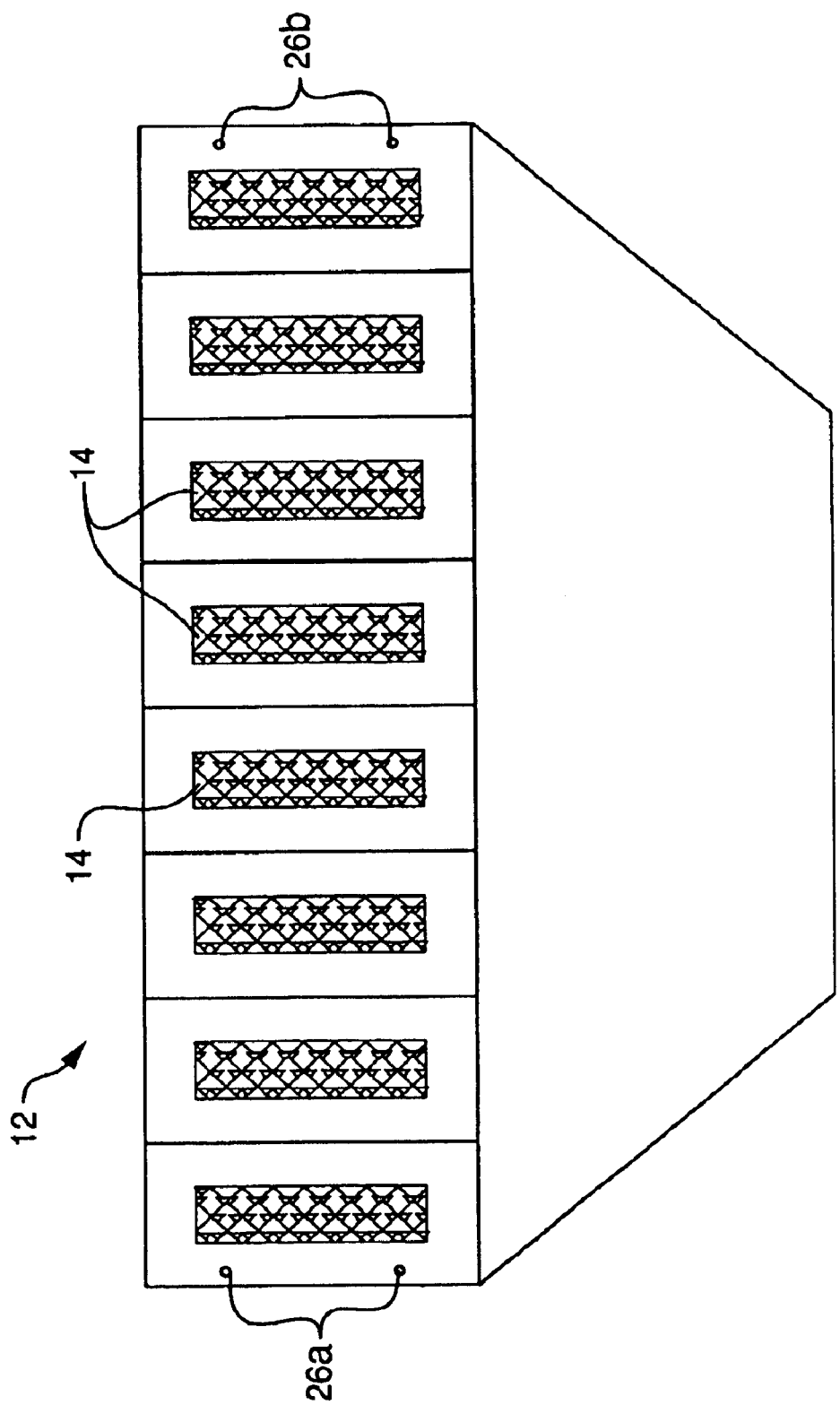
FIG. 15 is a planar representation of a wrap element with attachment mechanisms according to the invention.

In FIG. 15 a planar representation of a wrap element 12 is shown schematically. The wrap element can have closures 26A, 26B at its ends and also includes a set of gripping elements or surfaces that are designed to contact and secure the device to the heart. In practice, more than two closure elements are preferably to effect closure and various other closure mechanisms (including the gripping elements described herein) can be used to fit the wrap element to the surface of the heart. Although the placement of the gripping arrays is shown in FIG. 15 as being symmetrical, it should be clear that other arrangements of the gripping elements are possible and may, in some instances, be preferable. For example, the gripping elements and/or arrays can be disposed in an arrangement that follows the natural contours of the heart and ensures that the gripping elements come into contact with one or more major surfaces of the heart or regions that are more likely to provide strong adherence. Similarly, the gripping elements can be arranged in manner that avoids major blood vessels. It can even be preferable, in some instances, to construct a "custom" wrap design in which the wrap element and the arrays of gripping elements are specifically shaped and disposed to match the contours and surface features of an individual patient's heart.

Figure 16:
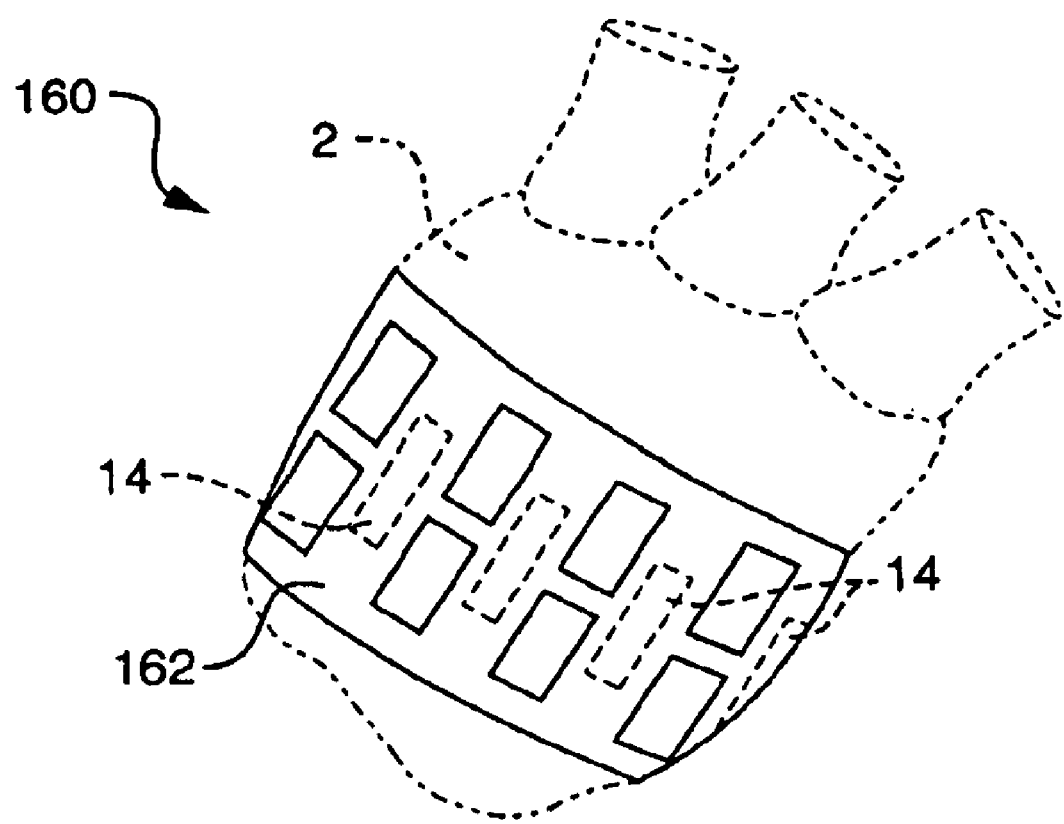
FIG. 16 is a schematic, perspective view of a passive cardiac assist device with attachment mechanisms according to another aspect of the invention.

FIG. 16 shows a passive extra-cardiac assist device 160 for use in supporting a a hypertrophied heart 2. The assist device 160 can include a mesh wrap element 162 and a series of gripping element arrays 14, according to the invention. The mesh 162 of device 160 serves to prevent expansion of the heart beyond a defined volumetric limit while the arrays of gripping elements 14 ensure that the passive wrap remains in the desired location.

The gripping elements of the present invention are particularly useful to connect a wide variety of medical devices to the heart and, unlike convention attachment mechanisms, the gripping elements disclosed herein can actually achieve enhanced attachment over time. Unlike glues that can degrade overtime or sutures that can tear, it should be appreciated that the arrays of gripping elements can not only provide a rapid initial attachment mechanism but over time are capable of "settling in" or becoming more attached as the heart moves.

While specific details of extra-cardiac assist systems with "heart-gripping" attachment mechanisms have been illustrated, it will be understood that other embodiments may be formed employing the principles of this invention. For example, the gripping elements and attachment mechanisms of this invention can be useful in attaching medical devices to other body organs or tissue structures, such as the bladder, pancreas or stomach.

What is claimed is:

1. In a heart wrap medical device adapted to surround at least a portion of a natural heart and having an inner heart contacting surface, the improvement comprising:
   an attachment array for attaching the heart wrap medical device to a natural heart comprising:
      at least one substrate that forms part of a heart-contacting surface of the heart wrap medical device; and
      a plurality of gripping elements disposed upon the substrate, wherein each of the gripping elements include an elongate element having a curved distal end constructed and arranged to penetrate, and lodge in, cardiac tissue.

2. The device of claim 1 wherein each of the elongate elements has a proximal end that is joined to the substrate.

3. The device of claim 1 wherein each of the elongate elements further comprises a barbed distal end.

4. In a heart wrap medical device adapted to surround at least a portion of a natural heart and having an inner heart contacting surface, the improvement comprising:
   an attachment array for attaching the heart wrap medical device to a natural heart comprising:
      at least one substrate that forms part of a heart-contacting surface of the heart wrap medical device; and
      a plurality of hooks disposed upon the substrate wherein the hooks are sized to penetrate no more than 500 micrometers into cardiac tissue, whereby damage to cardiac tissue is lessened.

5. The device of claim 3 wherein the hooks are sized to penetrate less than 300 micrometers into cardiac tissue, whereby damage to cardiac tissue is lessened.

6. In a heart wrap medical device adapted to surround at least a portion of a natural heart and having an inner heart contacting surface, the improvement comprising:
   an attachment array for attaching the heart wrap medical device to a natural heart comprising:
      at least one substrate that forms part of a heart-contacting surface of the heart wrap medical device; and
      a plurality of gripping elements each of which includes an elongate element having a curved distal end wherein the elongate elements has an uncurled height ranging from about 0.2 millimeters to about 3.0 millimeters, whereby damage to cardiac tissue is lessened.

7. The device of claim 6 wherein the elongate element has an uncurled height ranging from about 0.5 millimeters to about 1.5 millimeters, whereby damage to cardiac tissue is lessened.

8. In a heart wrap medical device adapted to surround at least a portion of a natural heart and having an inner heart contacting surface, the improvement comprising:
   an attachment array for attaching the heart wrap medical device to a natural heart comprising:
      at least one substrate that forms part of a heart-contacting surface of the heart wrap medical device; and
      a plurality gripping elements each of which includes an elongate element disposed upon the substrate wherein the elongate elements further comprises a curved distal end.

9. The device of claim 8 wherein the curved distal end has a radius ranging from about 100 micrometers to about 500 micrometers.

10. In a heart wrap medical device adapted to surround at least a portion of a natural heart and having an inner heart contacting surface, the improvement comprising:
   an attachment array for attaching the heart wrap medical device to a natural heart comprising:
      at least one substrate that forms part of a heart-contacting surface of the heart wrap medical device; and
      a plurality of gripping elements disposed upon the substrate wherein the gripping elements are hooks that are oriented in a pattern that restricts movement of the device in at least one direction to prevent detachment and permits movement in another direction to permit detachment.

11. The device of claim 10 wherein the gripping elements are hooks that are oriented in a pattern that restricts translatory motion in at least one direction.

12. The device of claim 10 wherein the gripping elements are hooks that are oriented in a pattern that restricts rotational motion in at least one direction.

13. A heart wrap medical device for placement on at least a portion of a natural heart comprising:
   a device body adapted to contact at least a portion of a heart;
   at least one substrate on the device body that contacts the natural heart; and
   at least one array of gripping elements disposed on a cardiac-contacting surface of the device to engage the heart during use, wherein the gripping elements each include an elongate element extending from the cardiac-contacting surface, each elongate element having a curved distal end constructed and arranged to penetrate, and lodge in, cardiac tissue.

14. The device of claim 13 wherein each of the elongate elements has a proximal end that is joined to the cardiac-contacting surface.

15. The device of claim 14 wherein the elongate elements further comprise a barbed distal end.

16. The device of claim 13 wherein a plurality of arrays are disposed in spaced apart relationship along the cardiac-contacting surface of the device.

17. The device of claim 13 wherein the device includes a sensor.

18. The device of claim 13 wherein the device is an extra-cardiac assist device.

19. The device of claim 13 wherein the device is an active, extra-cardiac, assist device.

20. The device of claim 13 wherein the device is a passive, extra-cardiac, assist device.

21. A heart wrap medical device for placement on at least a portion of a natural heart comprising,
   a device body adapted to contact at least a portion of a heart,
   at least one substrate on the device body that contacts the natural heart; and
   at least one array of gripping elements disposed on a cardiac-contacting surface of the device to engage the heart during use, each of which includes a hook wherein the hook is sized to penetrate no more than 500 micrometers into cardiac tissue, whereby damage to cardiac tissue is lessened.

22. The device of claim 21 wherein the hook is sized to penetrate less than 300 micrometers into cardiac tissue, whereby damage to cardiac tissue is lessened.

23. A heart wrap medical device for placement on at least a portion of a natural heart comprising,
   a device bode adapted to contact at least a portion of a heart,
   at least one substrate on the device body that contacts the natural heart, and
   at least one array of gripping elements disposed on a cardiac-contacting surface of the device to engage the heart during use, each of which includes a curved hook wherein the hook has an uncurled height ranging from about 0.2 millimeters to about 3.0 millimeters, whereby damage to cardiac tissue is lessened.

24. The device of claim 23 wherein the hook has an uncurled height ranging from about 0.5 millimeters to abut 1.5 millimeters, whereby damage to cardiac tissue is lessened.

25. A heart wrap medical device for placement on at least a portion of a natural heart comprising,
   device body adapted to contact at least a portion of a heart,
   at least fine substrate on the device body that contacts the natural heart; and
   at least one array of gripping elements disposed on a cardiac-contacting surface of the device to engage the heart during use, each of which includes an elongate element wherein the elongate element further comprises a curved distal end.

26. The device of claim 25 wherein the curved distal end has a radius ranging from about 100 micrometers to about 200 micrometers.

27. A heart wrap medical device for placement on at least a portion of a natural heart comprising:
   a device body adapted to contact at least a portion of a heart;
   at least one substrate on the device body that contacts the natural heart; and
   at least one array of gripping elements disposed on a cardiac-contacting surface of the device to engage the heart during use, wherein the gripping elements are hooks that are oriented in a pattern that restricts movement of the device in at least one direction to prevent detachment and permits movement in another direction to permit detachment.

28. The device of claim 27 wherein the gripping elements are hooks that are oriented in a pattern that restricts translatory motion in at least one direction.

29. The device of claim 27 wherein the gripping elements are hooks that are oriented in a pattern that restricts rotational motion in at least one direction.

30. An active extra-cardiac assist device comprising:
   a wrap element adapted to surround at least a portion of a heart, the wrap element forming a toroidal enclosure with an inner region;
   at least one inflatable chamber, which upon inflation decreases the size of the inner region of the wrap element to provide cardiac pumping assistance; and
   at least one array of gripping elements disposed on an inner surface of the wrap element to engage a heart during use, wherein the gripping elements include elongate an elongate element extending from an inner surface of the wrap element, each elongate element having a curved distal end constructed and arranged to penetrate, and lodge in, cardiac tissue.

31. The device of claim 30 wherein each of the elongate elements has a proximal end that is joined to the inner surface of the wrap element.

32. The device of claim 30 wherein the elongate elements further comprise a barbed distal end.

33. An active extra-cardiac assist device comprising:
   a wrap element adapted to surround at least a portion of a heart, the wrap element forming a toroidal enclosure with an inner region;
   at least one inflatable chamber, which upon inflation decreases the size of the inner region of the wrap element to provide cardiac pumping assistance; and
   at least one array of gripping elements each of which includes a hook wherein the hook is sized to penetrate no more than 500 micrometers into cardiac tissue, whereby damage to cardiac tissue is lessened.

34. The device of claim 33 wherein the hook is sized to penetrate less than 300 micrometers into cardiac tissue, whereby damage to cardiac tissue is lessened.

35. An active extra-cardiac assist device comprising:
   a wrap element adapted to surround at least a portion of a heart, the wrap element forming a toroidal enclosure with an inner region;
   at least one inflatable chamber, which upon inflation decreases the size of the inner region of the wrap element to provide cardiac pumping assistance; and
   at least one array of gripping elements each of which includes a curved hook wherein the hook has an uncurled height ranging from about 0.2 millimeters to about 3.0 millimeters, whereby damage to cardiac tissue is lessened.

36. The device of claim 35 wherein the hooks have an uncurled height ranging from about 0.5 millimeters to about 1.5 millimeters, whereby damage to cardiac tissue is lessened.

37. An active extra-cardiac assist device comprising:
   a wrap element adapted to surround at least a portion of a heart, the wrap element forming a toroidal enclosure with an inner region;
   at least one inflatable chamber, which upon inflation decreases the size of the inner region of the wrap element to provide cardiac pumping assistance; and at least one array of gripping elements each of which contains an elongate element wherein the elongate elements further comprises a curved distal end.

38. The device of claim 37 wherein the curved distal end has a radius ranging from about 100 micrometers to about 200 micrometers.

39. An active extra-cardiac assist device comprising:

a wrap element adapted to surround at least a portion of a heart, the wrap element forming a toroidal enclosure with an inner region;

at least one inflatable chamber, which upon inflation decreases the size of the inner region of the wrap element to provide cardiac pumping assistance; and at least one array of gripping elements, wherein the gripping elements are hooks that are oriented in a pattern that restricts movement of the device in at least one direction to prevent detachment and permits movement in another direction to permit detachment.

40. The device of claim 39 wherein the gripping elements are hooks that are oriented in a pattern that restricts translatory motion in at least one direction.

41. The device of claim 39 wherein the gripping elements are hooks that are oriented in a pattern that restricts rotational motion in at least one direction.

* * * * *